US006667037B1

(12) United States Patent
Ooms et al.

(10) Patent No.: US 6,667,037 B1
(45) Date of Patent: Dec. 23, 2003

(54) ISOLATED PEPTIDES WHICH BIND TO HLA-B35 MOLECULES, LARGER PEPTIDES WHICH CONTAIN THESE, NUCLEIC ACID MOLECULES ENCODING PEPTIDES, AND USES THEREOF

(75) Inventors: Annie Ooms, Liége (BE); Gérard De Giiovanni, Liége (BE); Sandra Morel, Brussels (BE); Benoît Van Den Eynde, Brussels (BE); Thierry Boon-Falleur, Brussels (BE)

(73) Assignees: Ludwig Institute for Cancer Research, New York, NY (US); Universite de Liege, Liege (BG)

(*) Notice: Subject to any disclaimer, the term of this patent is extended or adjusted under 35 U.S.C. 154(b) by 0 days.

(21) Appl. No.: 09/169,717

(22) Filed: Oct. 9, 1998

(51) Int. Cl.[7] .................. A61K 39/00; A61K 45/00; A61K 38/00; C07K 7/06
(52) U.S. Cl. ................. 424/185.1; 530/328; 424/278.1; 514/15
(58) Field of Search ............ 530/328; 514/15; 424/185.1, 278.1

(56) References Cited

U.S. PATENT DOCUMENTS

| | | | |
|---|---|---|---|
| 4,898,814 A | | 2/1990 | Kwon |
| 5,487,974 A | | 1/1996 | Boon-Falleur et al. |
| 5,633,234 A | * | 5/1997 | August et al. |
| 5,744,316 A | | 4/1998 | Lethe et al. |
| 5,747,271 A | | 5/1998 | Boon-Falleur et al. |
| 5,843,688 A | | 12/1998 | Wolfel et al. |
| 6,069,001 A | * | 5/2000 | Van Den Eynde et al. |

OTHER PUBLICATIONS

Mason,et al., HLA Class I Region Sequences, 1998, Tissue Antigens 51: 417–466 (1998), pp. 417, 418, 458 and 464.
Ramensee, et al., "MHC Ligands and Peptide Motifs: First Listing", Immunogenetics 41: 178–228 (1995), p. 201.
Bouchard, Brigitte, et al., "Induction of Pigmentation in Mouse Fibroplasts by Expression of Hyman Tyrosinase cDNA", J.Exp. Med. 169: 2029–2042 (1989).
Degiovanni, Gerard, et al., "Antigenic Heterogeneity of a Human Melanoma Tumor Detected by Autologous CTL Clones", Eur.J. Immunol 18:671–676 (1988).
Kwon, et al., "Isolation and Sequence of a cDNA Clone for Human Tyrosinase that Maps at the Mouse c–Albino Locus", Proc.Natl. Acad.Sci. USA 84: 7473–7477 (1987).
Brichard, Vincent, et. al. J. Exp. Med. 178:489–495 (1993).

* cited by examiner

*Primary Examiner*—Christina Chan
*Assistant Examiner*—F. Pierre VanderVegt
(74) *Attorney, Agent, or Firm*—Fulbright & Jaworski

(57) ABSTRACT

The invention relates to peptides which bind to HLA-B35 molecules, leading to recognition and lysis of the resulting complexes by cytolytic T cells. Also a part of the invention are nucleic acid molecules which encode these peptides, and uses of each of these. The molecules are derived, in some cases, from tyrosinase, and portions of the tyrosinase molecule and portions of nucleic acid molecules which encode tyrosinase are also a part of the invention.

4 Claims, No Drawings

SEQUENCE LISTING

<160> NUMBER OF SEQ ID NOS: 39

<210> SEQ ID NO 1
<211> LENGTH: 9
<212> TYPE: PRT
<213> ORGANISM: Homo sapiens
<220> FEATURE:

<400> SEQUENCE: 1

Leu Pro Ser Ser Ala Asp Val Glu Phe
 1               5

<210> SEQ ID NO 2
<211> LENGTH: 9
<212> TYPE: PRT
<213> ORGANISM: Homo sapiens
<220> FEATURE:
<221> NAME/KEY: VARIANT
<222> LOCATION: 3 . . . 8
<223> OTHER INFORMATION: Xaa is any amino acid

<400> SEQUENCE: 2

Leu Pro Xaa Xaa Xaa Xaa Xaa Xaa Phe
 1               5

<210> SEQ ID NO 3
<211> LENGTH: 9
<212> TYPE: PRT
<213> ORGANISM: Homo sapiens
<220> FEATURE:
<221> NAME/KEY: VARIANT
<222> LOCATION: 4 . . . 8
<223> OTHER INFORMATION: Xaa is any amino acid

<400> SEQUENCE: 3

Leu Pro Ser Xaa Xaa Xaa Xaa Xaa Phe
 1               5

<210> SEQ ID NO 4
<211> LENGTH: 9
<212> TYPE: PRT
<213> ORGANISM: Homo sapiens
<220> FEATURE:
<221> NAME/KEY: VARIANT
<222> LOCATION: 3 and 5 . . . 8
<223> OTHER INFORMATION: Xaa is any amino acid

<400> SEQUENCE: 4

Leu Pro Xaa Ser Xaa Xaa Xaa Xaa Phe
 1               5

<210> SEQ ID NO 5
<211> LENGTH: 9
<212> TYPE: PRT
<213> ORGANISM: Homo sapiens
<220> FEATURE:
<221> NAME/KEY: VARIANT
<222> LOCATION: 3, 4 and 6 . . . 8
<223> OTHER INFORMATION: Xaa is any amino acid

<400> SEQUENCE: 5

Leu Pro Xaa Xaa Ala Xaa Xaa Xaa Phe
 1               5

<210> SEQ ID NO 6
<211> LENGTH: 9

```
<212> TYPE: PRT
<213> ORGANISM: Homo sapiens
<220> FEATURE:
<221> NAME/KEY: VARIANT
<222> LOCATION: 3 . . . 5, 7 and 8
<223> OTHER INFORMATION: Xaa is any amino acid

<400> SEQUENCE: 6

Leu Pro Xaa Xaa Xaa Asp Xaa Xaa Phe
 1               5

<210> SEQ ID NO 7
<211> LENGTH: 9
<212> TYPE: PRT
<213> ORGANISM: Homo sapiens
<220> FEATURE:

<400> SEQUENCE: 7

Glu Ala Asp Pro Thr Gly His Ser Tyr
 1               5

<210> SEQ ID NO 8
<211> LENGTH: 9
<212> TYPE: PRT
<213> ORGANISM: Homo sapiens
<220> FEATURE:

<400> SEQUENCE: 8

Ser Ala Tyr Gly Glu Pro Arg Lys Leu
 1               5

<210> SEQ ID NO 9
<211> LENGTH: 9
<212> TYPE: PRT
<213> ORGANISM: Homo sapiens
<220> FEATURE:

<400> SEQUENCE: 9

Glu Val Asp Pro Ile Gly His Leu Tyr
 1               5

<210> SEQ ID NO 10
<211> LENGTH: 9
<212> TYPE: PRT
<213> ORGANISM: Homo sapiens
<220> FEATURE:

<400> SEQUENCE: 10

Phe Leu Trp Gly Arg Pro Ala Leu Val
 1               5

<210> SEQ ID NO 11
<211> LENGTH: 10
<212> TYPE: PRT
<213> ORGANISM: Homo sapiens

<400> SEQUENCE: 11

Met Glu Val Asp Pro Ile Gly His Leu Tyr
 1               5                  10

<210> SEQ ID NO 12
<211> LENGTH: 9
<212> TYPE: PRT
<213> ORGANISM: Homo sapiens

<400> SEQUENCE: 12
```

```
Ala Ala Arg Ala Val Phe Leu Ala Leu
  1               5
```

```
<210> SEQ ID NO 13
<211> LENGTH: 8
<212> TYPE: PRT
<213> ORGANISM: Homo sapiens

<400> SEQUENCE: 13
```

```
Tyr Arg Pro Arg Pro Arg Arg Tyr
  1               5
```

```
<210> SEQ ID NO 14
<211> LENGTH: 10
<212> TYPE: PRT
<213> ORGANISM: Homo sapiens

<400> SEQUENCE: 14
```

```
Ser Pro Ser Ser Asn Arg Ile Arg Asn Thr
  1               5                  10
```

```
<210> SEQ ID NO 15
<211> LENGTH: 10
<212> TYPE: PRT
<213> ORGANISM: Homo sapiens

<400> SEQUENCE: 15
```

```
Val Leu Pro Asp Val Phe Ile Arg Cys Val
  1               5                  10
```

```
<210> SEQ ID NO 16
<211> LENGTH: 9
<212> TYPE: PRT
<213> ORGANISM: Homo sapiens

<400> SEQUENCE: 16
```

```
Glu Glu Lys Leu Ile Val Val Leu Phe
  1               5
```

```
<210> SEQ ID NO 17
<211> LENGTH: 9
<212> TYPE: PRT
<213> ORGANISM: Homo sapiens

<400> SEQUENCE: 17
```

```
Glu Glu Lys Leu Ser Val Val Leu Phe
  1               5
```

```
<210> SEQ ID NO 18
<211> LENGTH: 10
<212> TYPE: PRT
<213> ORGANISM: Homo sapiens

<400> SEQUENCE: 18
```

```
Ala Cys Asp Pro His Ser Gly His Phe Val
  1               5                  10
```

```
<210> SEQ ID NO 19
<211> LENGTH: 10
<212> TYPE: PRT
<213> ORGANISM: Homo sapiens

<400> SEQUENCE: 19
```

```
Ala Arg Asp Pro His Ser Gly His Phe Val
  1               5                  10
```

<210> SEQ ID NO 20
<211> LENGTH: 9
<212> TYPE: PRT
<213> ORGANISM: Homo sapiens

<400> SEQUENCE: 20

Ser Tyr Leu Asp Ser Gly Ile His Phe
 1               5

<210> SEQ ID NO 21
<211> LENGTH: 9
<212> TYPE: PRT
<213> ORGANISM: Homo sapiens

<400> SEQUENCE: 21

Ser Tyr Leu Asp Ser Gly Ile His Phe
 1               5

<210> SEQ ID NO 22
<211> LENGTH: 9
<212> TYPE: PRT
<213> ORGANISM: Homo sapiens

<400> SEQUENCE: 22

Met Leu Leu Ala Val Leu Tyr Cys Leu
 1               5

<210> SEQ ID NO 23
<211> LENGTH: 9
<212> TYPE: PRT
<213> ORGANISM: Homo sapiens

<400> SEQUENCE: 23

Tyr Met Asn Gly Thr Met Ser Gln Val
 1               5

<210> SEQ ID NO 24
<211> LENGTH: 9
<212> TYPE: PRT
<213> ORGANISM: Homo sapiens

<400> SEQUENCE: 24

Tyr Met Asn Gly Thr Met Ser Gln Val
 1               5

<210> SEQ ID NO 25
<211> LENGTH: 9
<212> TYPE: PRT
<213> ORGANISM: Homo sapiens

<400> SEQUENCE: 25

Ala Phe Leu Pro Trp His Arg Leu Phe
 1               5

<210> SEQ ID NO 26
<211> LENGTH: 9
<212> TYPE: PRT
<213> ORGANISM: Homo sapiens

<400> SEQUENCE: 26

Ser Glu Ile Trp Arg Asp Ile Asp Phe
 1               5

```
<210> SEQ ID NO 27
<211> LENGTH: 9
<212> TYPE: PRT
<213> ORGANISM: Homo sapiens
<220> FEATURE:

<400> SEQUENCE: 27

Tyr Glu Ile Trp Arg Asp Ile Asp Phe
 1               5

<210> SEQ ID NO 28
<211> LENGTH: 15
<212> TYPE: PRT
<213> ORGANISM: Homo sapiens
<220> FEATURE:

<400> SEQUENCE: 28

Gln Asn Ile Leu Leu Ser Asn Ala Pro Leu Gly Pro Gly Phe Pro
 1               5                  10                  15

<210> SEQ ID NO 29
<211> LENGTH: 15
<212> TYPE: PRT
<213> ORGANISM: Homo sapiens
<220> FEATURE:

<400> SEQUENCE: 29

Asp Tyr Ser Tyr Leu Gln Asp Ser Asp Pro Asp Ser Phe Gln Asp
 1               5                  10                  15

<210> SEQ ID NO 30
<211> LENGTH: 10
<212> TYPE: PRT
<213> ORGANISM: Homo sapiens
<220> FEATURE:

<400> SEQUENCE: 30

Glu Ala Ala Gly Ile Gly Ile Leu Thr Val
 1               5                  10

<210> SEQ ID NO 31
<211> LENGTH: 9
<212> TYPE: PRT
<213> ORGANISM: Homo sapiens
<220> FEATURE:

<400> SEQUENCE: 31

Ile Leu Thr Val Ile Leu Gly Val Leu
 1               5

<210> SEQ ID NO 32
<211> LENGTH: 9
<212> TYPE: PRT
<213> ORGANISM: Homo sapiens
<220> FEATURE:

<400> SEQUENCE: 32

Lys Thr Trp Gly Gln Tyr Trp Gln Val
 1               5

<210> SEQ ID NO 33
<211> LENGTH: 9
<212> TYPE: PRT
<213> ORGANISM: Homo sapiens
<220> FEATURE:

<400> SEQUENCE: 33
```

Ile Thr Asp Gln Val Pro Phe Ser Val
1               5

<210> SEQ ID NO 34
<211> LENGTH: 9
<212> TYPE: PRT
<213> ORGANISM: Homo sapiens
<220> FEATURE:

<400> SEQUENCE: 34

Tyr Leu Glu Pro Gly Pro Val Thr Ala
1               5

<210> SEQ ID NO 35
<211> LENGTH: 10
<212> TYPE: PRT
<213> ORGANISM: Homo sapiens
<220> FEATURE:

<400> SEQUENCE: 35

Leu Leu Asp Gly Thr Ala Thr Leu Arg Leu
1               5                   10

<210> SEQ ID NO 36
<211> LENGTH: 10
<212> TYPE: PRT
<213> ORGANISM: Homo sapiens
<220> FEATURE:

<400> SEQUENCE: 36

Val Leu Tyr Arg Tyr Gly Ser Phe Ser Val
1               5                   10

<210> SEQ ID NO 37
<211> LENGTH: 9
<212> TYPE: PRT
<213> ORGANISM: Homo sapiens
<220> FEATURE:

<400> SEQUENCE: 37

Leu Tyr Val Asp Ser Leu Phe Phe Leu
1               5

<210> SEQ ID NO 38
<211> LENGTH: 12
<212> TYPE: PRT
<213> ORGANISM: Homo sapiens
<220> FEATURE:

<400> SEQUENCE: 38

Lys Ile Ser Gly Gly Pro Arg Ile Ser Tyr Pro Leu
1               5                   10

<210> SEQ ID NO 39
<211> LENGTH: 529
<212> TYPE: PRT
<213> ORGANISM: Homo sapiens
<220> FEATURE:

<400> SEQUENCE: 39

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
                20                  25                  30

-continued

Lys Glu Cys Cys Pro Pro Trp Ser Gly Asp Arg Ser Pro Cys Gly Gln
         35                  40                  45

Leu Ser Gly Arg Gly Ser Cys Gln Asn Ile Leu Leu Ser Asn Ala Pro
     50                  55                  60

Leu Gly Pro Gln Phe Pro Phe Thr Gly Val Asp Asp Arg Glu Ser Trp
 65              70                  75                      80

Pro Ser Val Phe Tyr Asn Arg Thr Cys Gln Cys Ser Gly Asn Phe Met
                 85                  90                  95

Gly Phe Asn Cys Gly Asn Cys Lys Phe Gly Phe Trp Gly Pro Asn Cys
             100                 105                 110

Thr Glu Arg Arg Leu Leu Val Arg Arg Asn Ile Phe Asp Leu Ser Ala
         115                 120                 125

Pro Glu Lys Asp Lys Phe Phe Ala Tyr Leu Thr Leu Ala Lys His Thr
         130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
             165                 170                 175

Val Trp Met His Tyr Tyr Val Ser Met Asp Ala Leu Leu Gly Gly Ser
             180                 185                 190

Glu Ile Trp Arg Asp Ile Asp Phe Ala His Glu Ala Pro Ala Phe Leu
         195                 200                 205

Pro Trp His Arg Leu Phe Leu Leu Arg Trp Glu Gln Glu Ile Gln Lys
         210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                 245                 250                 255

Pro Thr Asn Pro Asn Leu Leu Ser Pro Ala Ser Phe Phe Ser Ser Trp
             260                 265                 270

Gln Ile Val Cys Ser Arg Leu Glu Glu Tyr Asn Ser His Gln Ser Leu
         275                 280                 285

Cys Asn Gly Thr Pro Glu Gly Pro Leu Arg Arg Asn Pro Gly Asn His
290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                 325                 330                 335

Asn Phe Ser Phe Arg Asn Thr Leu Glu Gly Phe Ala Ser Pro Leu Thr
             340                 345                 350

Gly Ile Ala Asp Ala Ser Gln Ser Ser Met His Asn Ala Leu His Ile
         355                 360                 365

Tyr Met Asn Gly Tyr Met Ser Gln Val Gln Gly Ser Ala Asn Asp Pro
         370                 375                 380

Ile Phe Leu Leu His His Ala Phe Val Asp Ser Ile Phe Glu Gln Trp
385                 390                 395                 400

Leu Gln Arg His Arg Pro Leu Gln Glu Val Tyr Pro Glu Ala Asn Ala
             405                 410                 415

Pro Ile Gly His Asn Arg Glu Ser Tyr Met Val Pro Phe Ile Pro Leu
             420                 425                 430

Tyr Arg Asn Gly Asp Phe Phe Ile Ser Ser Lys Asp Leu Gly Tyr Asp
         435                 440                 445

Tyr Ser Tyr Leu Gln Asp Ser Asp Pro Asp Ser Phe Gln Asp Tyr Ile

```
                    450                       455                       460
Lys Ser Tyr Leu Glu Gln Ala Ser Arg Ile Trp Ser Trp Leu Leu Gly
465                     470                 475                     480

Ala Ala Met Val Gly Ala Val Leu Thr Ala Leu Leu Ala Gly Leu Val
                485                 490                     495

Ser Leu Leu Cys Arg His Lys Arg Lys Gln Leu Pro Glu Glu Lys Gln
                500                 505                 510

Pro Leu Leu Met Glu Lys Glu Asp Tyr His Ser Leu Tyr Gln Ser His
        515                 520                 525

Leu
```

ISOLATED PEPTIDES WHICH BIND TO HLA-B35 MOLECULES, LARGER PEPTIDES WHICH CONTAIN THESE, NUCLEIC ACID MOLECULES ENCODING PEPTIDES, AND USES THEREOF

FIELD OF THE INVENTION

This invention relates to peptides which are presented by MHC molecules, leading to recognition by cytolytic T cells. More specifically, it relates to peptides which bind to HLA-B35 molecules, and are nonamers.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, *Science* 257:880 (1992); Fremont et al., *Science* 257:919(1992); Matsumura et al., *Science* 257:927 (1992); Latron et al., *Science* 257:964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogentics* 35:145 (1992); van der Bruggen et al., *Science* 254:1643 (1991), both of which are incorporated by reference for further information on this family of genes.

In U.S. Pat. No. 5,405,940, the disclosure of which is incorporated by reference, nonapeptides are taught which bind to the HLA-A1 molecule. The patent teaches that, given the known specificity of particular peptides for particular HLA molecules, one should expect a particular peptide to preferentially bind one particular HLA molecule, but not others. This is important, because different individuals possess different HLA phenotypes. As a result, while identification of a particular peptide as being a partner for a specific HLA molecule or class of HLA molecules has diagnostic and therapeutic ramifications, these are only relevant for individuals with that particular HLA phenotype. There is a need for further work in the area, because many cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., *EMBO J* 7:2715 (1988)). An early report of cDNA for the human enzyme is found in Kwon, U.S. Pat. No. 4, 898,814. A later report by Bouchard et al., *J. Exp. Med.* 169:2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

Various U.S. Patent Applications incorporated by reference herein, teach that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells.

For example, allowed patent application Ser. No. 08/583, 238, filed Jan. 5, 1996, now U.S. Pat. No. 5,843,688, teaches peptides which are derived from tyrosinase, and which complex to HLA-A2 and HLA-B44 molecules. Additional information on peptides derived from tyrosinase which are presented by HLA molecules may be found in U.S. Pat. No. 5,487,974, and patent applications Ser. No. 08/203,054, filed Feb. 28, 1994, Ser. No. 08/081,673, filed Jun. 23, 1993 and Ser. No. 07/994,928, filed Dec. 22, 1992, and now abandoned. All of these references are incorporated by reference.

It is known that HLA-B35 molecules present peptides, with the resulting complexes being recognized by CTLs. See, in this regard, allowed U.S. patent application Ser. No. 08/718,964, filed Sep. 26, 1996, now U.S. Pat. No. 5,932, 694 and incorporated by reference. Other information on presentation by HLA-B35 molecules may be found in, e.g., Rammensee, et al., *Immunogenetics* 41:171 (1995), page 207 in particular, incorporated by reference. Also see Mason, et al., *Tissue Antigens* 51:417–465 (1998) incorporated by reference. Page 458 lists the amino acid sequences for the known HLA-B35 alleles, and shows that there is a great deal of identity there between.

New peptides have been identified which bind to HLA-B35 molecules, and are then recognized by CTLs. It is these peptides, and their use, which constitute the invention.

While derived from tyrosinase, the peptides of the invention need not be derived therefrom, as will be clear to the skilled artisan, and which will be seen from the disclosure which follows.

DETAILED DESCRIPTION OF PREFERRED EMBODIMENTS

EXAMPLE 1

The melanoma cell line LG2-MEL, described by Degiovanni, et al., *Eur. J. Immunol.* 18:671–676 (1988), is recognized by autologous cytolytic T lymphocytes. At least three antigens are presented on its surface and are recognized by these CTLs; however, none of these antigens have been isolated or otherwise described. These experiments describe how the peptide recognized by "CTL 35-24" was identified.

First, in experiments not described herein, two monoclonal antibodies against HLA-B and HLA-C molecules were combined with CTL 35-24 and cell line LG2-MEL. These antibodies are described by Rebai, et al, *Tissue Antigens* 22:107–117 (1983), and Yang, et al., *Immunogenetics* 19:217–231 (1984) both of which are incorporated by reference. It was found that the antibodies inhibited lysis of LG2-MEL by CTL 35-24. Essentially, this was accomplished by adding dilutions of antibody (1/3–1/80) to the cytotoxicity assay. Since prior HLA typing had identified HLA-A24, A32, B35, B44, and Cw*04 as the HLA molecules that the melanoma cell line presents, it was clear that the presenting molecule was either B35, B44, or Cw*04.

It is well known that sublines of cancer cell lines can be derived, which present less than all of the HLA molecules of the parent line. One such subline of LG2-MEL, i.e. LG2-MEL 220, was known, which had lost expression of HLA-B35. CTL 35-24 failed to lyse this subline, suggesting that the presenting molecule is HLA-B35.

Subsequently, the cDNA for the HLA-B35 molecule was isolated, and sequenced, and found to be allelic subtype HLA-B*3503. This subtype differs marginally from the other known HLA subtypes, as can be seen from Mason et al., supra. Hence, it is believed that the allelic subtypes are equivalent for purposes of peptide presentation.

EXAMPLE 2

As indicated in the "BACKGROUND" section, supra, melanoma cells are known to express a number of genes which are either not expressed or are expressed only in a restricted number of normal cells. These genes include MAGE genes, BAGE, GAGE (1–6), RAGE (1–4), LAGE, PRAME, tyrosinase, Melan-A, NY-ESO-1, pme/17, CASP-8, MUM-1, and gp100. Experiments were carried out to determine if the antigen presented by the HLA-B35 molecule was processed from one of these genes. To do this, cDNA for each of the above was obtained, following standard methods, and vectors prepared. The vectors were used to transfect COS cells, which were also transfected with cDNA for the HLA-B*3503 molecule expressed by LG2-MEL. The cDNA used (i.e., cDNA for HLA-B*3503), was obtained from a cDNA library prepared from BB 49-SCCHN cells. This cell line is described by Mandruzzato, et al, *J. Exp. Med.* 186(5):785–793 (1997), incorporated by reference. The transfections were carried out using 50 ng of each construct, described supra, using the well known DEAE/dextran method. Twenty four hours after transfection, CTL 35-24 (1500 cells), was added, and TNF production was measured, 24 hours later, using standard methods. See Traversari, et al, *Immunogenetics* 35:145–152 (1992). Controls were used including cell line LG2-MEL 5-35 (positive control),and COS cells transfected with HLA-B*3503 alone, or the melanoma associated gene alone. Only those cells which expressed both tyrosinase and HLA-B*3503 stimulated TNF production.

EXAMPLE 3

Once tyrosinase was identified as the processed molecule, studies were undertaken to determine the identity of the peptide presented by HLA-B*3503. To do this, fragments of tyrosinase cDNA were prepared, following Wolfel, et al., *Eur. J. Immunol.* 24:759–764 (1994), and Brichard, et al., *Eur. J. Immunol.* 26:224–230 (1996), both of which are incorporated by reference, as well as U.S. Pat. No. 5,487,974, also incorporated by reference. SEQ ID NO: 1 in this patent is SEQ ID NO: 40 of this application.

The same TNF assay as is described in example 2, supra, was used, except fragments of tyrosinase cDNA, rather than complete cDNA molecules, were used. Three fragments were positive, and these corresponded to nucleotides 1–1086, 427–1134, and 703–1134 of the coding region of tyrosinase cDNA. A fragment corresponding to position 574–831 was negative, leading to the conclusion that nucleotides 831–1086 encoded for the presented antigen. These correspond to amino acids 270–362 of tyrosinase, whose amino acid sequence is known. This amino acid sequence was compared to known peptides, which bind to HLA-B*3501, and its binding motif, as described by Rammensee, et al., supra, incorporated by reference. This reference describes a binding motif for HLA-B35 which is a nonapeptide, where Pro is found at position 2, and Tyr is found at position 9. For decapeptides, Ramensee, et al, gives P2 and Y10 as anchors. HLA-B*3501 was used because no information was found in the art for HLA-B*3503. Ramensee et al. also gives Phe, Met, Leu, and Ile as auxiliary anchors for P9. The peptide defined by amino acid sequence LPSSADVEF (SEQ ID NO: 1) satisfies these requisites, and is found at amino acids 312–320 of tyrosinase. Its ability to stimulate lysis was tested by synthesizing the peptide, adding it to autologous lymphoblastoid cell line LG2-EBV which expresses HLA-B*3503, and then adding CTL 35-24. Cell line HA7-EBV was also tested. This line expresses HLA B*3501. A $^{51}$Cr release assay was used, wherein cells were incubated with varying concentrations of the peptide of SEQ ID NO: 1. See U.S. Pat. No. 5,519,117, incorporated by reference, for details of the assay. The $^{51}$Cr labeled cells were incubated for 30 minutes with the peptide, after which CTL 35-24 was added, in an effector (CTL) target (LG2-EBV) ratio of 5:1. The $^{51}$Cr release was measured after 3.5 hours.

The results show that the peptide provoked lysis of both types of cells, indicating that the peptide bound to both HLA-B*3501 and B*3503. A dose of 1nM of peptide gave half maximal lysis of LG2-EBV cells and a dose of about 10 nM of peptide gave half maximal lysis of HA7-EBV cells.

The foregoing examples describe the invention, which are peptides which bind to HLA-B35 molecules. These peptides are of formula Leu Pro Xaa Xaa Xaa Xaa Xaa Xaa Phe (SEQ ID NO: 2). Within this genus of peptides, those with position 3 as Ser, position 4 as Ser, position 5 as Ala, or position 6 as Asp, are preferred (SEQ ID NOS: 3–6). Peptides in accordance with the invention may have one or more of positions 3–6 as defined above. Positions 7 and 8 may be any amiro acid. Also a part of the invention are peptides which correspond to the above referenced peptide, but are flanked at the N and C termini to no more than amino acids 270–312 and 321–362 of tyrosinase. In other words, peptides whose amino acids consist of no more than amino acids 270–311, concatenated to SEQ ID NO: 2, which is then concatenated to amino acids 321–362, respectively. Hence, peptides which consist of, e.g., amino acids 290–311 of tyrosinase, followed by SEQ ID NO: 2, followed by amino acids 321–340 of tyrosinase, are a part of the invention. Preferably, peptides no longer than about 16 amino acids and which comprise SEQ ID NO: 2 or SEQ ID NO: 1, or any of SEQ ID NOS: 4–6, are a part of the invention.

Also a facet of the invention are combinations of peptides which include at least the peptide of SEQ ID NO: 2, preferably one of the peptides of SEQ ID NOS: 1 and 3–6, together with one or more additional MHC or HLA binding peptides. It is known that individuals generally express six different HLA molecules on their cell surfaces. As the review of the art in the "BACKGROUND" section indicates, peptides which bind to other HLA molecules are known, as are other peptides which bind to HLA-B35 molecules. One can thus "customize" compositions comprising two or more MHC binding peptides, wherein at least one of these binding peptides is a peptide defined by SEQ ID NOS: 1–6.

Also a part of the invention are nucleic acid molecules which encode the peptides of the invention, such as a nucleic acid molecule consisting of nucleotides which encode no more than amino acids 270–362 of tyrosinase, and no less than a peptide as defined by SEQ ID NO: 2, or more preferably, one of SEQ ID NOS: 1 and 3–6. These nucleic acid molecules can be incorporated into expression vectors, and the nucleic acid molecules or vectors can be used to transform or transfect cells, cell lines, and cell strains, be these eukaryotic or prokaryotic. They can also be used in combination with nucleic acid molecules which encode an MHC molecule, such as an HLA-B35 molecule, such as HLA B*3501 or HLA-B*3503.

The peptides and nucleic acid molecules of the invention have various uses, which are also a part of the invention. For example, in addition to their usefulness in therapeutic applications, such as the generation of cytolytic T cells, either in vitro or in vivo, which specifically lyse pathogenic cells, the peptides can be used to identify HLA-B35 positive cells, or to remove HLA-B35 positive cells from mixtures containing such cells. The nucleic acid molecules can be used, inter alia, as probes to identify cells which are expressing tyrosinase.

Also a part of the invention is a multicomponent complex useful, e.g., in isolating cytolytic T cells specific for a particular target, from a sample. The complex comprises a first binding partner and a second binding partner,. wherein the first and second binding partner are specific for each other. These can be, e.g., avidin or streptavidin and biotin, an antibody or a binding portion of an antibody specific to biotin, and so forth. The key feature is that the second binding partner must be bound to a plurality of complexes of an MHC molecule, a β2 microglobulin molecule and a peptide which binds specifically to said MHC molecule, and the multicomponent complex must be labeled. The MHC molecules are preferably HLA molecules, such as HLA-B35 molecules, but, it will be understood by the artisan of ordinary skill that any HLA molecule could be used. With respect to the peptides of interest, many references, including review articles, U.S. and non-U.S. patents, and so forth describe peptides beyond SEQ ID NOS: 2–6 and their binding partner HLA molecule. All are encompassed by the invention. Exemplary peptides and their HLA molecule partners are presented later in this application.

Preferably, the second binding partner is biotin, but it may also be, e.g., an antibody which is specific for a component of the HLA/β2 microglobulin/peptide complex, such as an HLA specific antibody, or a β2 microglobulin specific antibody. Similarly, the first binding partner may be e.g., recombinant or naturally occurring protein L, recombinant or naturally occurring protein A, or even a second antibody. The complex can be in soluble form, or bound, e.g., to a removable solid phase, such as a magnetic bead.

The number of HLA/β2 microglobulin/peptide complexes in the large molecule of the invention may vary. It comprises at least two complexes, and preferably at least four, but more may be present as well.

The complex of binding partners and HLA/β2 microglobulin/peptide may be labeled, using any of the labels known to the art. Examples of fluorescent labels are given supra. Enzymatic labels, such as alkaline phosphatase, metal particles, colored plastics made of synthetic materials, radioactive labels, etc., may all be used.

A third binding partner may also be used, which binds, specifically, to the first binding partner. For example, if the first binding partner is streptavidin, and the second binding partner is biotin, then the third binding partner may be a streptavidin specific antibody. When three or more binding partners are used, the label referred to supra may be attached to any of the binding partners so long as engagement with the HLA/β2 microglobulin/peptide complexes is not impaired.

The complexes may be used, e.g., to identify or to isolate cytolytic T cells present in a sample, where these cells are specific for the HLA/β2 microglobulin/peptide complex. As the examples show, such cytolytic T cells bind to the immunocomplexes of the invention. In a preferred embodiment, the sample being tested is treated with a reactant which specifically binds to a cytolytic T cell, wherein said label provides a detectable signal. The sample, including labeled CTLs, is then contacted to the complex, where it binds, and can be separated via any of the standard, well known approaches to cell separation. Preferably, FACS is used, but other separation methodologies will be known to the skilled artisan as well. The peptide used is left to the needs of the skilled artisan, and will depend, e.g., on the nature of the specific MHC system under consideration, a table of exemplary, but no means the only, peptides for which CTLs are known, follows. These are also set forth in SEQ ID NOS: 7–38.

| Gene | MHC | Peptide | SEQ ID |
|---|---|---|---|
| MAGE-1 | HLA-A1 | EADPTGHSY | 7 |
|  | HLA-Cw16 | SAYGEPRKL | 8 |
| MAGE-3 | HLA-A1 | EVDPIGHLY | 9 |
|  | HLA-A2 | FLWGRPALV | 10 |
|  | HLA-B44 | MEVDPIGHLY | 11 |
| BAGE | HLA-Cw16 | AARAVFLAL | 12 |
| GAGE-1,2 | HLA-Cw16 | YRPRPRRY | 13 |
| RAGE | HLA-B7 | SPSSNRIRNT | 14 |
| GntV | HLA-A2 | VLPDVFIRC(V) | 15 |
| MUM-1 | HLA-B44 | EEKLIVVLF | 16 |
|  |  | EEKLSVVLF | 17 |
| CDK4 | HLA-A2 | ACDPHSGHFV | 18 |
|  |  | ARDPHSGHFV | 19 |
| β-catenin | HLA-A24 | SYLDSGIHF | 20 |
|  |  | SYLDSGIHF | 21 |
| Tyrosinase | HLA-A2 | MLLAVLYCL | 22 |
|  | HLA-A2 | YMNGTMSQV | 23 |
|  | HLA-A2 | YMNGTMSQV | 24 |
|  | HLA-A24 | AFLPWHRLF | 25 |
|  | HLA-B44 | SEIWRDIDF | 26 |
|  | HLA-B44 | YEIWRDIDG | 27 |
|  | HLA-DR4 | QMLLSNAPLGPGFP | 28 |
|  | HLA-DR4 | DYSYLQDSDPDSFQD | 29 |
| Melan-A[Mart-1] | HLA-A2 | (E)AAGIGILTV | 30 |
|  | HLA-A2 | ILTVILGVL | 31 |
| gp100[Pmel117] | HLA-A2 | KTWGQYWQV | 32 |
|  | HLA-A2 | ITDQVPFSV | 33 |
|  | HLA-A2 | YLEPGPVTA | 34 |
|  | HLA-A2 | LLDGTATLRL | 35 |
|  | HLA-A2 | VLYRYGSFSV | 36 |
| DAGE | HLA-A24 | LYVDSLFFL | 37 |
| MAGE-6 | HLA-Cw16 | KISGGPRISYPL | 38 |

Additional peptides may be found, e.g., in U.S. patent application Ser. Nos. 08/672,351, 08/669,590, 08/487,135, now U.S. Pat. No. 08/530,569, and Ser. Nos. 08/880,693, and 08/718,964, now U.S. Pat. No. 5,932,694, all of which are incorporated by reference.

A further aspect of the invention are so-called "mini genes" which carry information necessary to direct synthesis of peptides via cells into which the mini genes are transfected. Mini genes can be designed which encode one or more antigenic peptides, and are then transferred to host cell genomes via transfection with plasmids, or via cloning into vaccinia or adenoviruses. See, e.g., Zajac, et al., *Int. J. Cancer* 71:496 (1997), incorporated by reference.

The peptides of the invention may be combined with peptides from other tumor rejection antigens to form 'polytopes'. Exemplary peptides include those listed in the applications set forth supra.

Additional peptides which can be used are those described in the following references, all of which are incorporated by reference: U.S. Pat. Nos. 5,405,940; 5,487,974; 5,519,117; 5,530,096; 5,554,506; 5,554,724; 5,558,995; 5,585,461; 5,589,334; 5,648,226; and 5,683,886; PCT International Publication Nos. 92/20356; 94/14459; 96/10577; 96/21673; 97/10837; 97/26535; and 97/31017 as well as pending U.S. application Ser. No. 08/713,354. These peptides may also be combined with peptides that complex with MHC-Class II molecules, such as peptides derived from tumor rejection antigen precursors as is described in Ser. No. 08/927,015, now U.S. Pat. No. 6,021,464, and a continuation in part application to Knuth et al., Ser. No. 09/165,546 filed on Oct. 2, 1998, as a CIP of Ser. No. 09/062,422. This newly filed CIP is incorporated by reference.

Polytopes are groups of two or more potentially immunogenic or immune stimulating peptides, which can be joined together in various ways, to determine if this type of molecule will stimulate and/or provoke an immune response.

These peptides can be joined together directly, or via the use of flanking sequences. See Thompson et al. *Proc. Natl. Acad. Sci. USA* 92(13):5845–5849 (1995), teaching the direct linkage of relevant epitopic sequences. The use of polytopes as vaccines is well known. See, e.g., Gilbert et al., *Nat. Biotechnol.* 15(12): 1280–1284 (1997); Thompson et al., supra; Thompson et al., *J. Immunol.* 157(2):822–826 (1996); Tam et al., *J. Exp. Med.* 171(l):299–306 (1990) of which are incorporated by reference. The Tam reference in particular shows that polytopes, when used in a mouse model, are useful in generating both antibody and protective immunity. Further, the reference shows that the polytopes, when digested, yield peptides which can be and are presented by MHCs. Tam shows this by showing recognition of individual epitopes processed from polytope 'strings' via CTLs. This approach can be used, e.g., in determining how many epitopes can be joined in a polytope and still provoke recognition and also to determine the efficacy of different combinations of epitopoes. Different combinations may be 'tailor-made' for the patients expressing particular subsets of tumor rejection antigens. These polytopes can be introduced as polypeptide structures, or via the use of nucleic acid delivery systems. To elaborate, the art has many different ways available to introduce DNA encoding an individual epitope, or a polytope such as is discussed supra. See, e.g., Allsopp et al., *Eur. J. Immunol.* 26(8); 1951–1959 (1996), incorporated by reference. Adenovirus, pox-virus, Ty-virus like particles, plasmids, bacteria, etc., can be used. One can test these systems in mouse models to determine which system seems most appropriate for a given, parallel situation in humans. They can also be tested in human clinical trials.

Also a feature of the invention are compositions which comprise at least one of the peptides of the invention, in combination with at least one adjuvant. Such compositions can be used, e.g., to generate immune responses, preferably in humans, as part of a therapeutic regime, but also in subject non-human animals, to generate immune components which can then be used to treat humans, or diagnostically. The artisan of ordinary skill is familiar with such adjuvants, and thus these do not have to be set forth here.

These compositions can also include so-called co-stimulatory molecules. These are molecules which are proteins, or encode proteins, that interact with molecules on the surface of T cells, thereby co-stimulating a T cell already stimulated by formation of an MHC molecule/antigen/T cell receptor interaction. Such co-stimulatory molecules enhance antitumor immunity, and CTL proliferation. Exemplary of such co-stimulatory molecules are those known as "B7-1" and "B7-12," or CD80 and CD86, respectively. See Zhang, et al, *Proc. Natl. Acad. Sci. USA* 95(11):6284–6289 (1998), incorporated by reference.

Such co-stimulatory molecules can be combined with, e.g. interleukins, such as IL-6 and IL-12. See Gajewski, et al, *J. Immunol* 154:5637–5648 (1995). As noted, supra, the co-stimulatory molecules may be administered in the form of a nucleic acid molecule. Such an approach can be useful in connection with CTL expansion for adoptive transfer immunotherapy (Wang et al, *J. Immunother. Emphasis Tumor Immunol.* 19:1–8 (1996)). The requisite nucleic acid molecules can be administered in the form of "naked" DNA (Kim et al, *Nat. Biotechnol* 15(7):641–646 (1997)), as well as in the form of recombinant vectors, such as adenovirus and pox virus vectors. See Wendtner et al, *Gene Ther.* 4(7):726–735 (1997). All of these systems can be adapted so that the co-stimulatory molecule is expressed together with other molecules of choice, including the peptides, adjuvant molecules, and so forth.

In addition to the foregoing, antibodies can function as co-stimulatory molecules, as these can act as ligands to cell receptors, thereby costimulating the cell. The B7 molecules discussed supra are ligands for CD28 molecules. Hence, anti CD28 antibodies, be these polyclonal, monoclonal, humanized, etc., can all act in this fashion.

In addition to B7 molecules, lymphocyte function associated antigen-1 (LFA-1), CD40L and anti-CD40 antibodies can also be used as co-stimulatory molecules. These are all exemplary of the family of co-stimulatory molecules, and should not be regarded as the only possible alternatives.

Also a feature of the invention is the use of these peptides to determine the presence of cytolytic T cells in a sample. It was shown, supra, that CTLs in a sample will react with peptide/MHC complexes. Hence, if one knows that CTLs are in a sample, HLA-B35 positive cells can be "lysed" by adding the peptides of the invention to HLA-B35 positive cells, such as HLA-B*3503 positive cells, and then determining, e.g., radioactive chromium release, TNF production, etc. or any other of the methods by which T cell activity is determined. Similarly, one can determine whether or not specific tumor infiltrating lymphocytes ("TILs") are present in a sample, by adding one of the claimed peptides with HLA-B35 positive cells to a sample, and determining lysis of the HLA-B35 positive cells via, e.g., $^{51}$Cr release, TNF presence and so forth. In addition, CTL may be detected by ELI-SPOT analysis. See for example Schmittel et al. (1997). *J. Immunol. Methods* 210:167–174 and Lalvani et al. *J. Exp. Med.* 126:859 (1997) or by FACS analysis of fluorogenic tetramer complexes of MHC Class I/peptide (Dunbar et al. (1998), *Current Biology* 8:413–416. All are incorporated by reference.

Of course, the peptides may also be used to provoke production of CTLs. As was shown, supra, CTL precursors develop into CTLs when confronted with appropriate complexes. By causing such a "confrontation" as it were, one may generate CTLs. This is useful in an in vivo context, as well as ex vivo, for generating such CTLs.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated peptide which binds to an HLA-B*3503 molecule and consists of the amino acid sequence set forth in SEQ ID NO: 1.

2. A composition comprising the isolated peptide of claim 1, and an adjuvant.

3. A composition comprising the isolated peptide of claim 1, and at least one other HLA binding peptide.

4. The composition of claim 3, wherein said at least one other HLA binding peptide bind to an HLA Class II molecule.

* * * * *